United States Patent
Lopez et al.

(10) Patent No.: US 8,922,094 B2
(45) Date of Patent: Dec. 30, 2014

(54) MICROELECTROMECHANICAL (MEMS) MANIPULATORS FOR CONTROL OF NANOPARTICLE COUPLING INTERACTIONS

(75) Inventors: Omar Daniel Lopez, Chicago, IL (US); Gary Wiederrecht, Elmhurst, IL (US); David J. Gosztola, Naperville, IL (US); Derrick C. Mancini, Riverside, IL (US)

(73) Assignee: UChicago Argonne, LLC, Chicago, IL (US)

( * ) Notice: Subject to any disclaimer, the term of this patent is extended or adjusted under 35 U.S.C. 154(b) by 720 days.

(21) Appl. No.: 13/022,353

(22) Filed: Feb. 7, 2011

(65) Prior Publication Data

US 2011/0192248 A1 Aug. 11, 2011

Related U.S. Application Data

(60) Provisional application No. 61/302,396, filed on Feb. 8, 2010.

(51) Int. Cl.
*H02N 1/00* (2006.01)
(52) U.S. Cl.
CPC .................................... *H02N 1/008* (2013.01)
USPC .......................................... 310/309; 310/300
(58) Field of Classification Search
CPC ............................... H02N 1/008; H01L 23/53
USPC ................... 310/309, 300; 74/490.09, 490.1; 200/181; 257/183; 977/872
IPC ....................................................... H01L 23/53
See application file for complete search history.

(56) References Cited

U.S. PATENT DOCUMENTS

| 5,753,911 | A | * | 5/1998 | Yasuda et al. | 850/1 |
| 5,914,553 | A | * | 6/1999 | Adams et al. | 310/309 |
| 2002/0061662 | A1 | * | 5/2002 | Boggild | 438/800 |
| 2007/0267939 | A1 | * | 11/2007 | Borovic et al. | 310/309 |

* cited by examiner

*Primary Examiner* — Quyen Leung
*Assistant Examiner* — Thomas Truong
(74) *Attorney, Agent, or Firm* — Foley & Lardner LLP (57) ABSTRACT

A nanopositioning system for producing a coupling interaction between a first nanoparticle and a second nanoparticle. A first MEMS positioning assembly includes an electro-static comb drive actuator configured to selectively displace a first nanoparticle in a first dimension and an electrode configured to selectively displace the first nanoparticle in a second dimensions. Accordingly, the first nanoparticle may be selectively positioned in two dimensions to modulate the distance between the first nanoparticle and a second nanoparticle that may be coupled to a second MEMS positioning assembly. Modulating the distance between the first and second nanoparticles obtains a coupling interaction between the nanoparticles that alters at least one material property of the nanoparticles applicable to a variety of sensing and control applications.

13 Claims, 10 Drawing Sheets

MICROELECTROMECHANICAL (MEMS) MANIPULATORS FOR CONTROL OF NANOPARTICLE COUPLING INTERACTIONS

CROSS REFERENCE TO RELATED PATENT APPLICATIONS

The present application claims priority to U.S. Provisional Patent Application No. 61/302,396, filed Feb. 8, 2010, the contents of which are incorporated herein by reference in their entirety.

STATEMENT OF GOVERNMENT INTEREST

The United States Government claims certain rights in this invention pursuant to Contract No. W-31-109-ENG-38 between the United States Government and the University of Chicago and/or pursuant to DE-AC02-06CH11357 between the United States Government and UChicago Argonne, LLC representing Argonne National Laboratory.

FIELD OF THE INVENTION

The present invention relates generally to the field of controlled nanoparticle interaction. More particularly, the present invention relates to microelectromechanical (MEMS) manipulators and methods of using a MEMS manipulator to control nanoparticle location to produce coupling interactions that modulate one or more properties of the nanoparticles.

BACKGROUND OF THE INVENTION

This section is intended to provide a background or context to the invention that is, inter alia, recited in the claims. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

A common approach to making closely spaced metal nanoparticles is through advanced lithographic methods. Electron beam lithography is frequently used to make nanostructures on the scale of a few 10 s of nanometers in size and with similar spacing between nanostructures. However, prior efforts in this regard suffer from the inability to reliably produce features on this length scale with high precision. Defects in shape, size, and/or spacing generally arise when producing nanostructures on the scale of 10 nm in length using lithographic techniques. Currently, lithography techniques cannot reliably fabricate nanostructures with a spacing of 10 nm or less. Furthermore, lithography yields static structures and does not allow for optimization of optical and electronic coupling between the nanoparticles, as real-time control over the distance between nanoparticles is not achievable.

As a result of these limitations, attempts have been made to use rough mechanical means to essentially push two particles together. [J. Merlein et al., Nature Photonics 2, 230 (2008)] Electron beam lithography has been used to create two nanoparticles with an initial spacing of about 85 nm. Subsequently, an atomic force microscope tip is used to push one of the particles closer to the other. This is a crude method to move nanoparticles closer, and suffers from deficiencies such as damaging the nanoparticles, the substantial time needed to accomplish movement, and a complete lack of reversibility in the degree of coupling between the nanoparticles. Attempts at applying MEMS to move two "swords" of silicon coated Au structures to near contact have also been made [IEEE Transducers 2009 conference (Jun. 21-25, 2009)]. Here, the silicon swords had micron lengths and included coarse position control.

Achieving nanoparticle separation on the scale of less than 10 nm is generally beyond the reliable capability of modern nanofabrication tools. In addition to the nanoparticle spacing issue, the ability to modulate this distance in a reversible manner would be of value for a wide range of next generation nanoscale devices. For example, controlled coupling of nanoparticles could be used as a switching framework to control optical and electrical energy flow in nanoscale devices. Another example that could benefit from this technology would be a sensor where strongly interacting fields of the involved nanoparticles produce shifts in the absorption and scattering resonances of the particles. Another benefit of close nanoparticle coupling would be the gain in the sensitivity of spectroscopies, including surface enhanced Raman spectroscopy (SERS), that result from large field confinement and enhancement effects in the gaps between nanoparticles. For example, by positioning molecules within this small region, molecular spectroscopy of a single molecule can be achievable. Precise control of the distance between nanoparticles is also needed to manage the efficiency of bow-tie nanoantennas. Nanoantenna structures are best known for providing a mechanism for focusing light into the nanoscale gap between conductors. It is expected that these structures could ultimately provide optical readout for on chip nanophotonic logic or light routing devices.

SUMMARY

It thus would be beneficial to obtain closely spaced nanoparticles that produce coupling interactions that modulate properties of the nanoparticles, for example, electronic and optical properties. This is a challenging goal, because the degree of interaction between nanoparticles generally increases with decreasing distance between the nanoparticles. The degree of interaction is generally nonlinearly dependant on the distance. In other words, a small distance between the nanoparticles is desired, and a distance of less than 10 nm is preferred.

MEMS technology may be applied to dynamically control the distance between nanoparticles and, as a consequence, control their interaction. Several MEMS devices and different types of actuation mechanisms (electrostatic, thermal, piezoelectric, optical and magnetic) can be used for this purpose. Electrostatic actuation can provide fast and very precise position control. The advanced MEMS positioning device of one embodiment of the present invention comprises an array of electrostatically actuated comb-drive MEMS actuators coupled to a positioning element such as a micron-size needle. The comb-drive actuators include a releasable comb portion and an anchored comb portion. The MEMS positioning device may further include a restoring force element coupled to the comb-drive actuator and a portion of the micro-needle. The nanoparticle and/or nanostructure may be disposed on the micro-needle, and in one preferred embodiment, is located at the distal tip of the micro-needle.

The configuration of the present system enables real-time adjustment of nanoparticle position to modulate the gap between nanoparticles within a precision of less than about 1 nm. In operation, when a voltage is applied to the array of comb-drive actuators, the releasable comb portion moves toward the anchored comb portion. This motion displaces the coupled micro-needle along a first axis and induces a mechanical deformation of the coupled restoring force element. The mechanical deformation of the restoring force element provides a restoring force useful to control the displacement of the coupled micro-needle. The MEMS positioning device may further include a lateral electrode to induce lateral motion of the micro-needle along a second axis. The second axis may be substantially orthogonal with respect to the first axis. As such, the array of comb-drives provide motion control in a first dimension and the lateral electrodes allow perpendicular displacement of the micro-needle in a second dimension. In this way, the relative position of the nanoparticles may be independently modulated in two-degrees of freedom. Modulation in additional degrees of freedom may further be achieved by including additional electrodes and/or positioning elements associated with the positioning device.

In an embodiment, a first MEMS positioning device and a second MEMS position device are arranged with respect to each other such that the nanoparticles disposed on the respective micro-needles may be brought into close proximity, thereby decreasing the distance between the nanoparticles with respect to an initial position. In a preferred embodiment, the nanoparticles may be brought within less than about 10 nm of each other. In another preferred embodiment, the nanoparticles may be brought within less than about 1 nm of each other.

Accordingly, an object of the present system is to achieve nanoparticle-nanoparticle spacing of less than about 10 nm. According to another object of the present system, electrically controllable and tunable spacing between nanoparticles in two-degrees of freedom is provided. Yet another object of the present system is to obtain positioning capabilities of a plurality of nanoparticles with precision better than about 1 nm. Still another object, is to provide a method for achieving these capabilities.

In one set of embodiments, a nanopositioning system for producing a coupling interaction between a first nanostructure and a second nanostructure comprises a first MEMS positioning assembly. The first MEMS positioning assembly includes a first static comb drive actuator and a first dynamic comb drive actuator. The first static comb drive actuator is configured to selectively displace the first dynamic comb drive actuator along a first axis in relation to the first static comb drive actuator upon application of a voltage to the first static comb-drive actuator. The first MEMS positioning assembly further includes a first restoring force element having a first end and a second end. The first end of the restoring force element is operatively attached to the first dynamic comb drive actuator, and the second end is attached to the first static comb drive actuator. The first MEMS positioning assembly also includes a first positioning electrode configured to selectively displace the first dynamic comb drive actuator along a second axis in relation to the first static comb drive actuator upon application of a voltage to the first positioning electrode. A first nanostructure is operatively connected to the first dynamic comb drive actuator. Accordingly, the first nanostructure is selectively positionable along the first axis and along the second axis, modulating a distance between the first nanostructure and the second nanostructure to obtain a coupling interaction that alters at least one property of the first nanostructure and the second nanostructure.

In another set of embodiments, a method for selectively modifying a property of a plurality of nanoparticles through a coupling interaction between the plurality of nanoparticles comprises providing a first nanoparticle, providing a first MEMS positioning assembly having a first positioning portion. The first MEMS positioning assembly is configured to selectively displace the first positioning portion along a first axis in response to a first voltage and to selectively displace the first positioning portion along a second axis substantially normal to the first axis in response to a second voltage. The method further comprises coupling the first nanoparticle to the first positioning portion, providing a second nanoparticle spaced a distance from the first nanoparticle, and modulating the distance between the first nanoparticle and the second nanoparticle by displacement of the first positioning portion along at least one of the first axis and the second axis to obtain a coupling interaction between the first nanoparticle and the second nanoparticle. The coupling interaction alters at least one property of the first nanoparticle and the second nanoparticle.

In a further set of embodiments, an electrostatic nanopositioning system for modulating a distance between a first nanostructure and a second nanostructure to control an interaction between the first nanostructure and the second nanostructure comprises a first nanopositioner configured to receive a first nanoparticle, a second nanopositioner configured to receive a second nanoparticle spaced a distance from the first nanoparticle so as to cause a coupling interaction between the first nanoparticle and the second nanoparticle. Each of the first nanopositioner and the second nanopositioner include a positioning portion selectively moveable along a respective first path by an array of electrostatic comb drive actuators and selectively moveable along a respective second path by an electrode. Each of the first nanopositioner and the second nanopositioner further include a restoring force element coupled to the positioning portion. The restoring force element is deformable in response to movement of the positioning portion along the respective first path. The coupling interaction between the first nanostructure and the second nanostructure is controllable by modulating the distance between the first nanostructure and the second nanostructure by movement of at least one of the first nanostructure and the second nanostructure along at least one of the respective first paths and the respective second paths.

These and other advantages and features of the invention, together with the organization and manner of operation thereof, will become apparent from the following detailed description when taken in conjunction with the accompanying drawings, wherein like elements have like numerals throughout the several drawings described below.

BRIEF DESCRIPTION OF THE DRAWINGS

FIGS. 3A-3B are scanning electron microscope (SEM) images showing a detailed perspective view of a pair of MEMS nanoparticle positioning systems of FIG. 1 with a pair of attached nanodots (FIG. 3A)

DETAILED DESCRIPTION OF EMBODIMENTS

Figure 1:
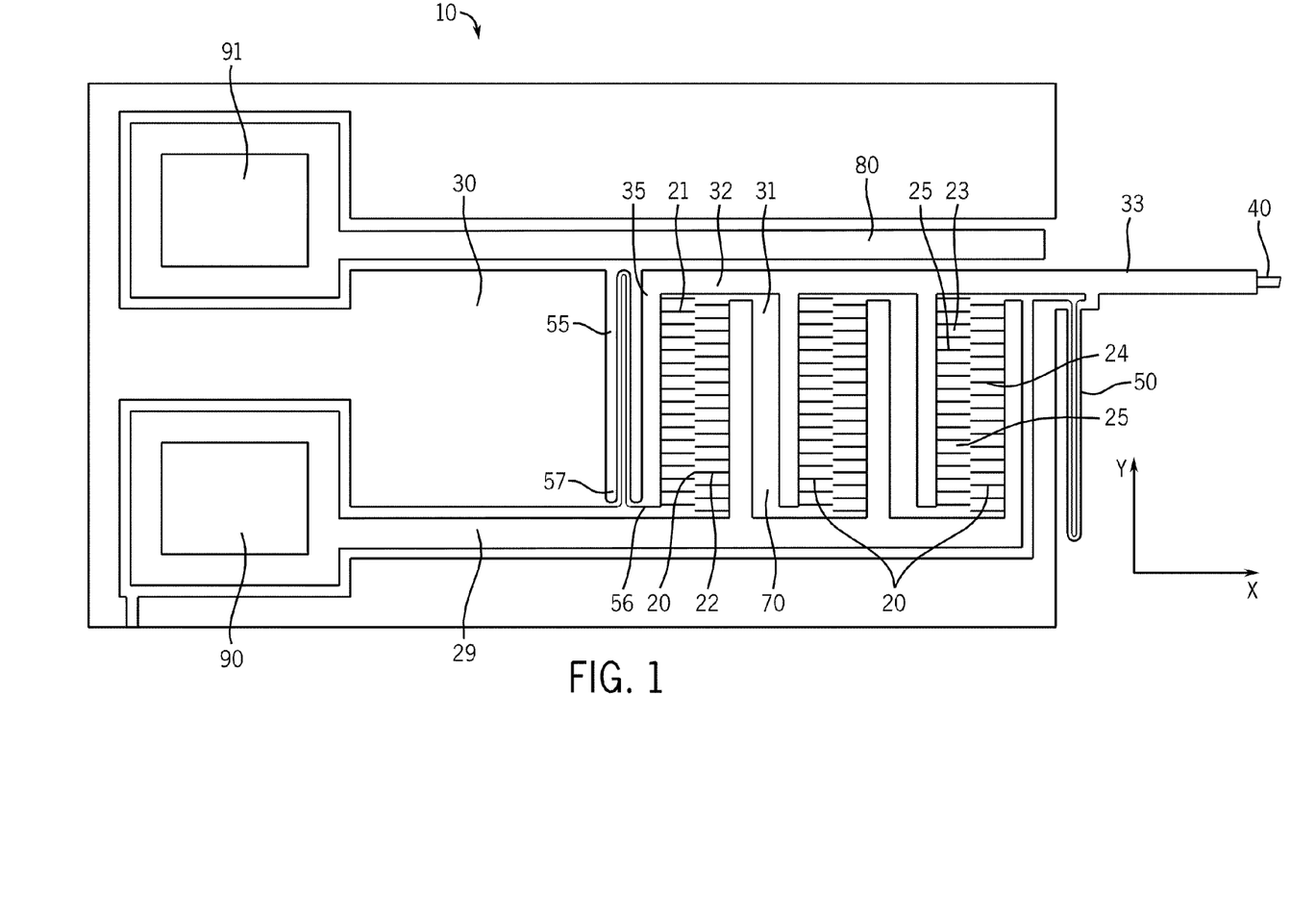
FIG. 1 is a perspective view of a MEMS nanoparticle positioning system constructed in accordance with an embodiment of the present invention and shown in a first position.

An exemplary nanoparticle MEMS positioning system 10 shown in FIG. 1 comprises one or more voltage controlled actuators detailed below. In other embodiments, a thermal, a piezoelectric, an optical and/or a magnetic MEMS positioning system may be used. The voltage controlled actuator may be configured to work in concert with a restoring force element to produce a nanopositioning device with better than 1 nm positioning resolution in a plurality of dimensions. FIGS. 1-7 illustrate a nanoparticle MEMS positioning system 10 constructed in accordance with an embodiment of the present invention. The MEMS positioning system 10 comprises an array of electrostatically actuated comb-drive actuators 20 coupled to at least one positioning element such, as a micron-size micro-needle 40. The array of comb-drive actuators 20 include a releasable comb portion 21 and an anchored comb portion 22. The MEMS positioning system 10 may further include a first restoring force element 50 operatively coupled to the releasable comb portion 21 and operatively coupled to the anchored comb portion 22. A nanoparticle and/or nanostructure 60 may be disposed on a portion of the micro-needle 40, and in an embodiment, is located proximate a distal tip 42 of the micro-needle 40. At least a portion of the MEMS positioning system 10 may be located on a substrate 70.

Figure 2:
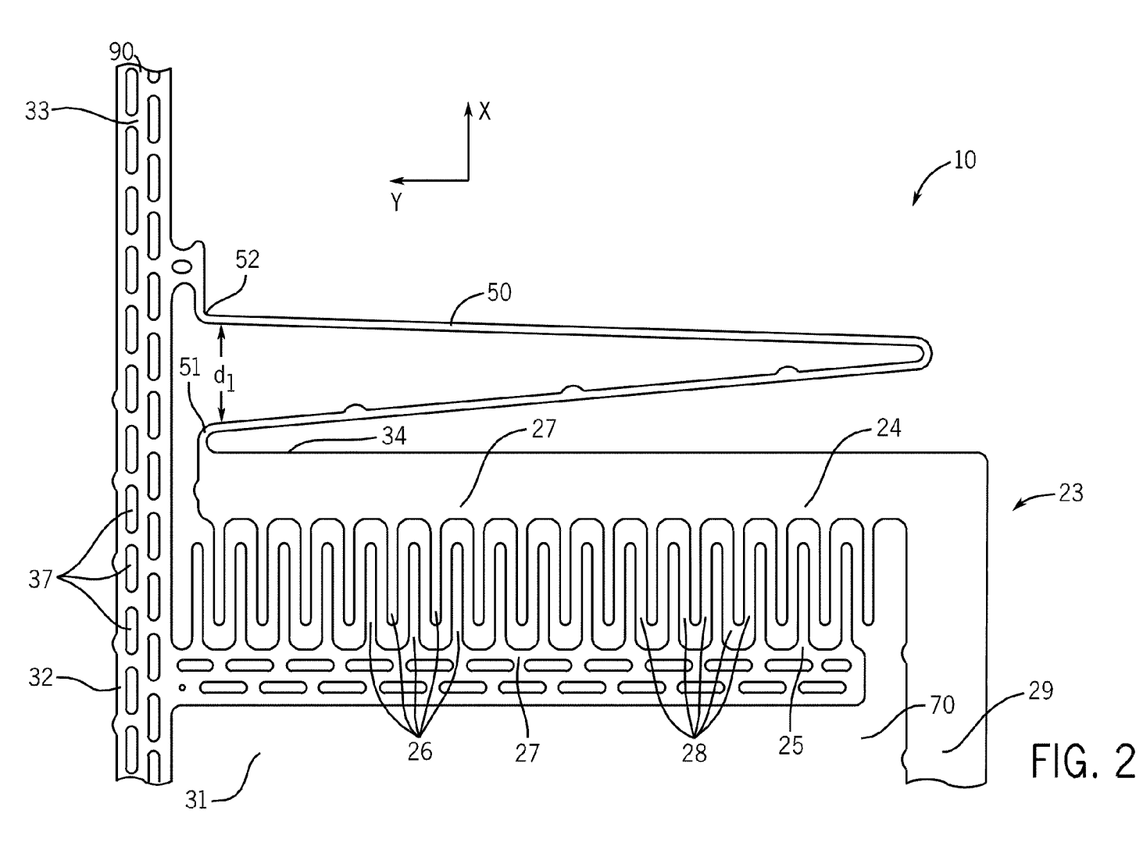
FIG. 2 is a detailed top view of a portion of the MEMS nanoparticle positioning system of FIG. 1 and shown in a second position.

With reference to FIGS. 1 and 2, the array of comb-drive actuators 20 includes a plurality of actuator elements 23. Each of the plurality of actuator elements 23 comprises a static comb portion 24 and a dynamic comb portion 25 associated with the static comb portion 24. Each of the static comb portion 24 and the dynamic comb portion 25 is characterized by a plurality of comb teeth 26 coupled to a comb base 27 and a plurality of comb openings 28 disposed between each of the plurality of comb teeth 26. Each of the plurality of comb teeth 26 extend substantially perpendicular from the comb base 27 in a plane proximate the substrate 70. Each comb base 27 associated with the static comb portion 24 is coupled to a static link member 29 that connects each of the static comb portions 24. As depicted in FIG. 1, the static link member 29 may be substantially parallel to the plurality of comb teeth 26 associated with the anchored comb portion 22. The static link member 29 further electrically couples each of the static comb portions 24 to a first electrical contact 90. The array of the comb-drive actuators 20 may be fabricated from, for example, silicon.

The dynamic comb portion 25 is disposed in an actuator opening 31 in a base portion 30 of the MEMS positioning system 10. Each of the comb bases 27 associated with a dynamic comb portion 25 is coupled to a dynamic link 32. The dynamic link 32 and each of the comb bases 27 that are associated with the dynamic comb potion 25 may include a plurality of openings 37 to minimize the mass of the releasable comb portion 21. The dynamic link 32 may include a boom 33 that extends away from the base portion 30. As depicted in FIG. 1, the boom 33 extends in a plane substantially parallel to the substrate 70 and substantially parallel to the plurality of comb teeth 26. However, in other embodiments, the boom 33 may be configured to achieve any desired position and/or displacement profile.

Figure 3A:
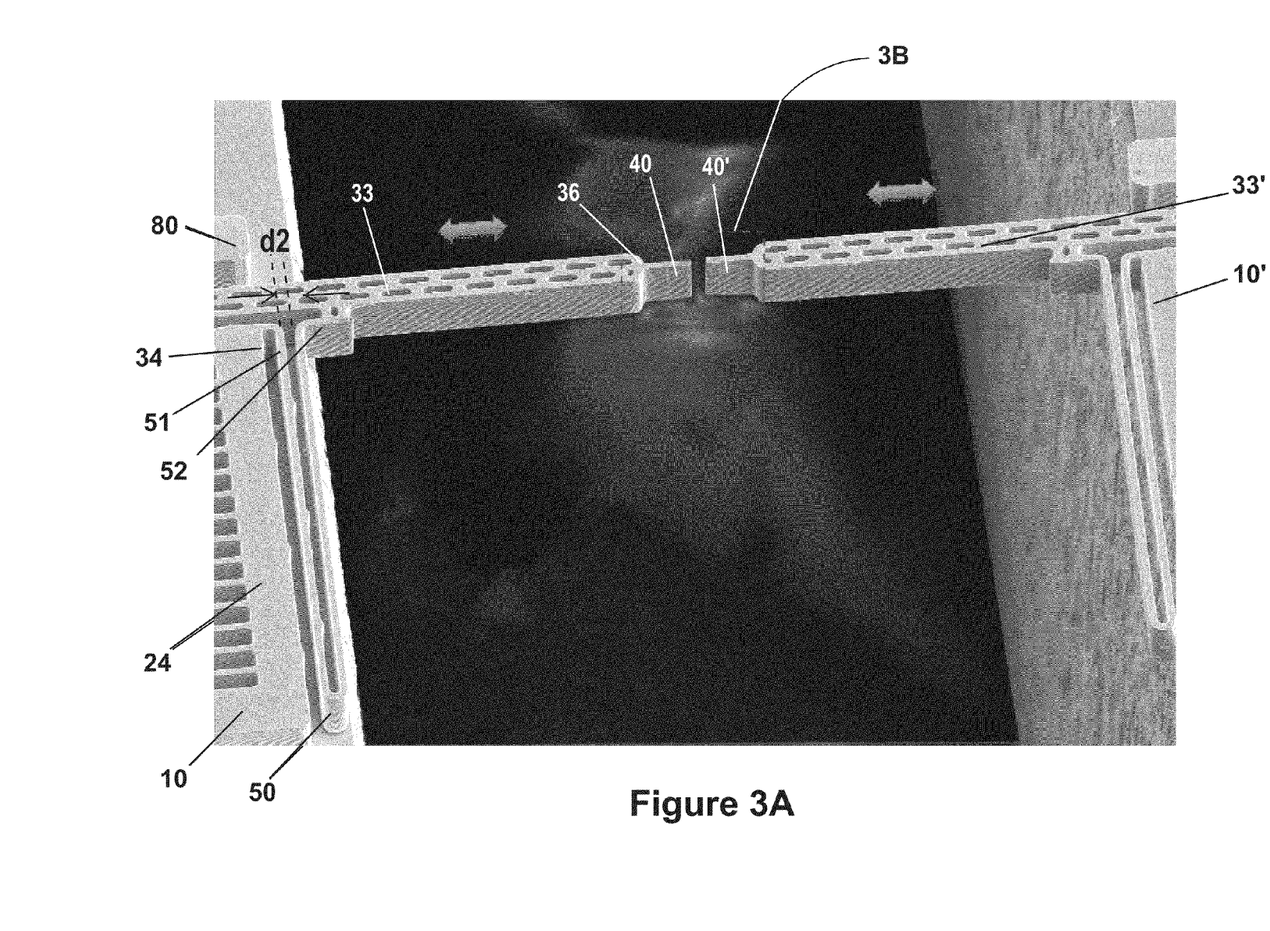
Figure 6:
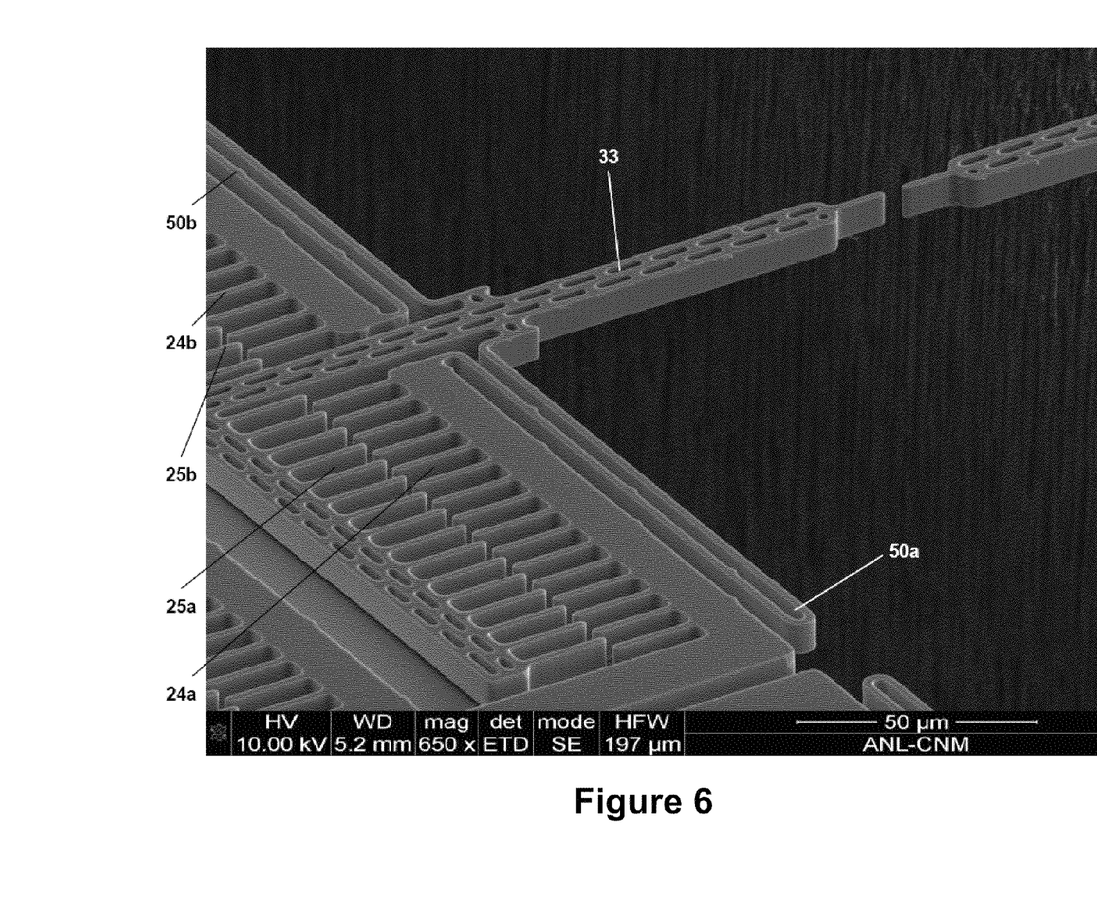
FIG. 6 is a SEM image of a MEMS nanoparticle positioning system constructed in accordance with a second embodiment of the present invention.

With reference to FIGS. 2 and 3A, a first restoring force element 50 may operatively couple the boom 33 and the static comb portion 24. As depicted, the first restoring force element 50 comprises an elongated "U" spring element with a static comb end 51 and a boom end 52. However, in various embodiments, the first restoring force element 50 may comprise other configurations. As shown in FIG. 2, the static comb end 51 is coupled to a leading edge 34 of the static comb portion 24. The boom end 52 is coupled to the boom 33. As explained in detail below, the first restoring force element 50 moderates the displacement of the boom 33 and the attached micro-needle 40. FIG. 2 depicts the first restoring force element 50 in an extended configuration with a first lateral distance d1 between the static comb end 51 and the boom end 52. FIG. 3A shows the first restoring force element 50 in a retracted configuration with a second distance d2, less than d1, between the static comb end 51 and the boom end 52. The first restoring force element 50 may be configured such that the retracted configuration is the natural position of the first restoring force element 50. FIG. 6 shows another embodiment of the MEMS positioning system 10 having a centrally located boom 33 disposed between a first static comb portion 24a and first dynamic comb portion 25a and a second static comb portion 24b and second dynamic comb portion 25b. In this embodiment, a pair of first restoring force elements 50a and 50b are provided and associated with opposite lateral sides of the boom 33.

By applying a voltage to the MEMS positioning system 10 the electrostatically actuated comb-drive actuators 20 move the nanopositioners closer together or further apart along a substantially linear first axis. In particular, applying a voltage to the first electrical contact 90 the dynamic comb portion 25 moves generally along the X axis as shown in FIGS. 1 and 2 relative to the static comb portion 24. FIG. 2 shows the MEMS positioning system 10 in a fully extended orientation where the comb teeth 26 of the dynamic comb portion 25 are partially received in the comb openings 28 of the static comb portion 24. In this orientation, the first restoring force element 50 is extended and the boom 33 and micro-needle 40 are extended away from the static comb portion 24. FIG. 1 shows the MEMS positioning system 10 in a fully retracted orientation where the comb teeth 26 of the dynamic comb portion 25 lie outside the comb openings 28 of the static comb portion 24. In this orientation, the first restoring force element 50 is retracted and the boom 33 and micro-needle 40 translated toward the static comb portion 24.

The MEMS positioning system 10 is reversible. That is, the MEMS positioning system 10 is selectively moveable between the orientations of FIGS. 1 and 2. The MEMS positioning system 10 may be further be positioned at any intermediate orientation with respect to the orientations depicted in FIGS. 1 and 2. Accordingly, a nanostructure coupled to the MEMS positioning system 10 may be selectively positioned with a high degree of precision in a first dimension substantially defined by the X axis. In an embodiment, the MEMS positioning system 10 is configured to provide adjustable position control of an attached nanoparticle to within about 1 nm or better resolution. Precise and adjustable positioning permits customized control of coupling interactions between two or more nanoparticles 60 for a variety of applications.

As shown in FIG. 1, the MEMS positioning system 10 may further include a second restoring force element 55. The second restoring force element 55, as depicted, couples the dynamic comb portion 25 to the base portion 30. The second restoring force element 55 may be configured substantially similar to first restoring force element 50. For example, in FIG. 1, the second restoring force element 55 comprises an elongated "U" spring element with a dynamic comb end 56 and a base end 57. However, the second restoring force element 55 may comprise other configurations. As shown in FIG. 1, the dynamic comb end 56 is coupled to a trailing edge 35 of the dynamic comb portion 25. The base end 57 is coupled to the base portion 30. The second restoring force element 55 works in conjunction with the first restoring force element 50 to moderate the displacement of the boom 33 and the attached micro-needle 40.

The MEMS positioning system 10 may also include a lateral electrode 80. As shown in FIG. 1, the lateral electrode 80 is located proximate at least a portion of the dynamic link 32 and may be substantially parallel to the dynamic link 32. Alternatively, the lateral electrode 80 may be located near the boom 33 or another location where it may act on the dynamic comb portion 25. The lateral electrode 80 is electrically coupled to a second electrical contact 91. The lateral electrode 80 is capable of producing lateral motion of the dynamic comb portion 25, including the boom 33 and the micro-needle 40. In other words, application of a voltage to the lateral electrode 80 causes a displacement substantially in the plane of and substantially normal to the axial displacement of the dynamic link 32. In general, the MEMS positioning system 10 is configured such that the range of lateral displacement is less than the range of the axial displacement. However, fine control of the position of MEMS positioning system 10, and any coupled nanostructure, simultaneously in two dimensions (along the X and Y axes) is achieved through electrical control of the electrostatically actuated comb-drive actuators 20 and the lateral electrode 80. Position control in additional dimensions (e.g., along the Z axis and/or rotations about one or more axes) may be achieved by associating additional electrodes or other positioning elements with the dynamic comb portion 25 and/or the MEMS positioning system 10 generally.

Figure 3B:
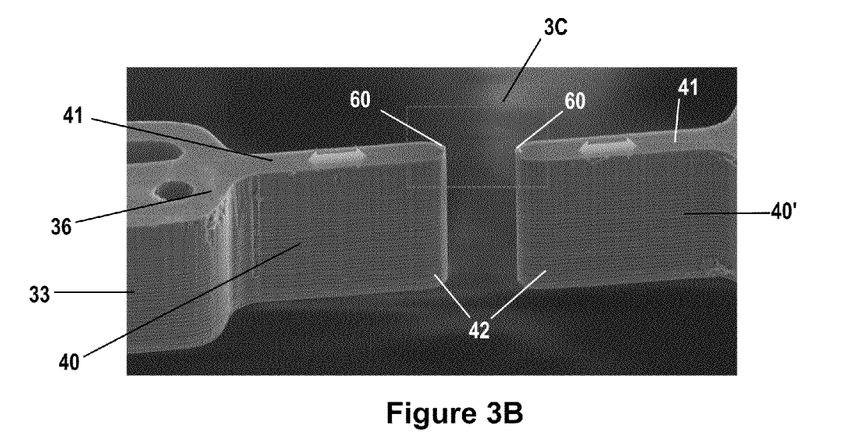
FIG. 3B is a detailed and magnified view showing a portion of the MEMS nanoparticle positioning systems of FIG. 3A.

With reference to FIGS. 3A and 3B, the micro-needle 40 may be coupled to a distal end 36 of the boom 33. The micro-needle 40 may comprise various configurations as necessitated by the application of the MEMS positioning system 10. However, as depicted, the micro-needle 40 is a narrow member that extends substantially coaxially from a distal end 36 of the boom 33. The micro-needle 40 and the boom 33 may be constructed from a single member or the micro-needle 40 may be coupled to the boom 33 using fabrication and/or attachment techniques known in the art. In various embodiments, the micro-needle 40 may be eliminated entirely.

Figure 3C:
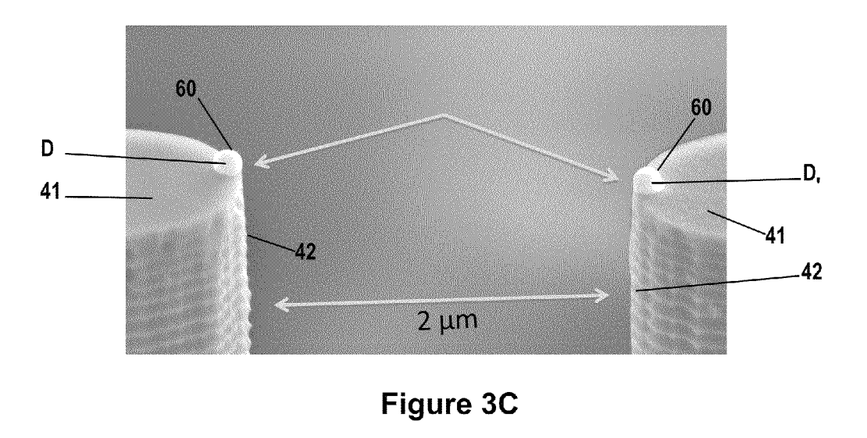
FIG. 3C is a further magnified view showing a portion of the MEMS nanoparticle positioning systems of FIG. 3B.

A nanostructure 60 as shown in FIGS. 3B and 3C may be disposed on one or more surfaces of the micro-needle 40. For example, a nanodot, nanosphere, nanorod, nanoplate, nanotriangle, nanopyramids, and other structures may be operatively and/or directly coupled to the micro-needle 40. Additionally, the various nanostructures may be disposed on a portion of the boom 33. As described below, the configuration of the nanostructure may be selected in view of the particular application or other parameter or material property. As shown in FIGS. 3B and 3C, a nanodot D (or D') may be located on an upper surface 41 of the micro-needle 40.

Figure 4A:
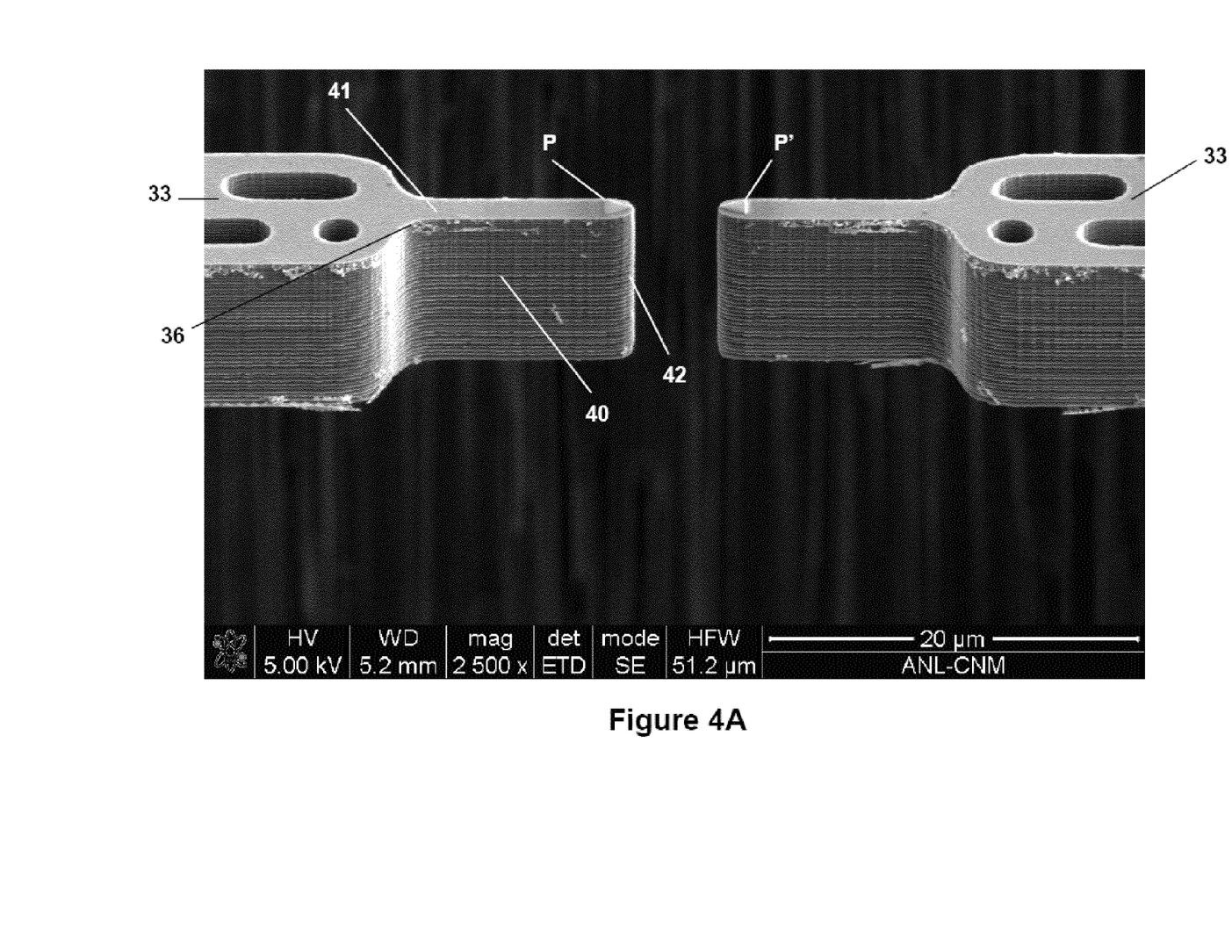
FIG. 4A is a detailed SEM image of a pair of MEMS nanoparticle positioning systems of FIG. 1 with a pair of attached nanopyramids and FIG. 4B is a detailed and magnified SEM image showing a portion of the MEMS nanoparticle positioning systems of FIG. 4A.
Figure 4B:
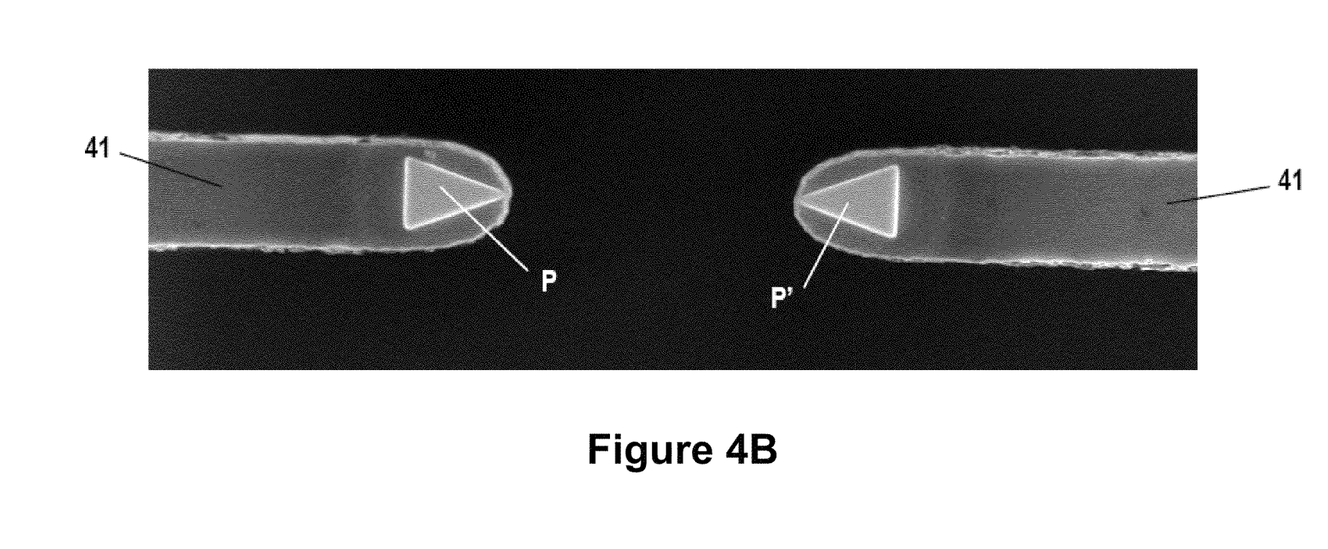
Figure 5A:
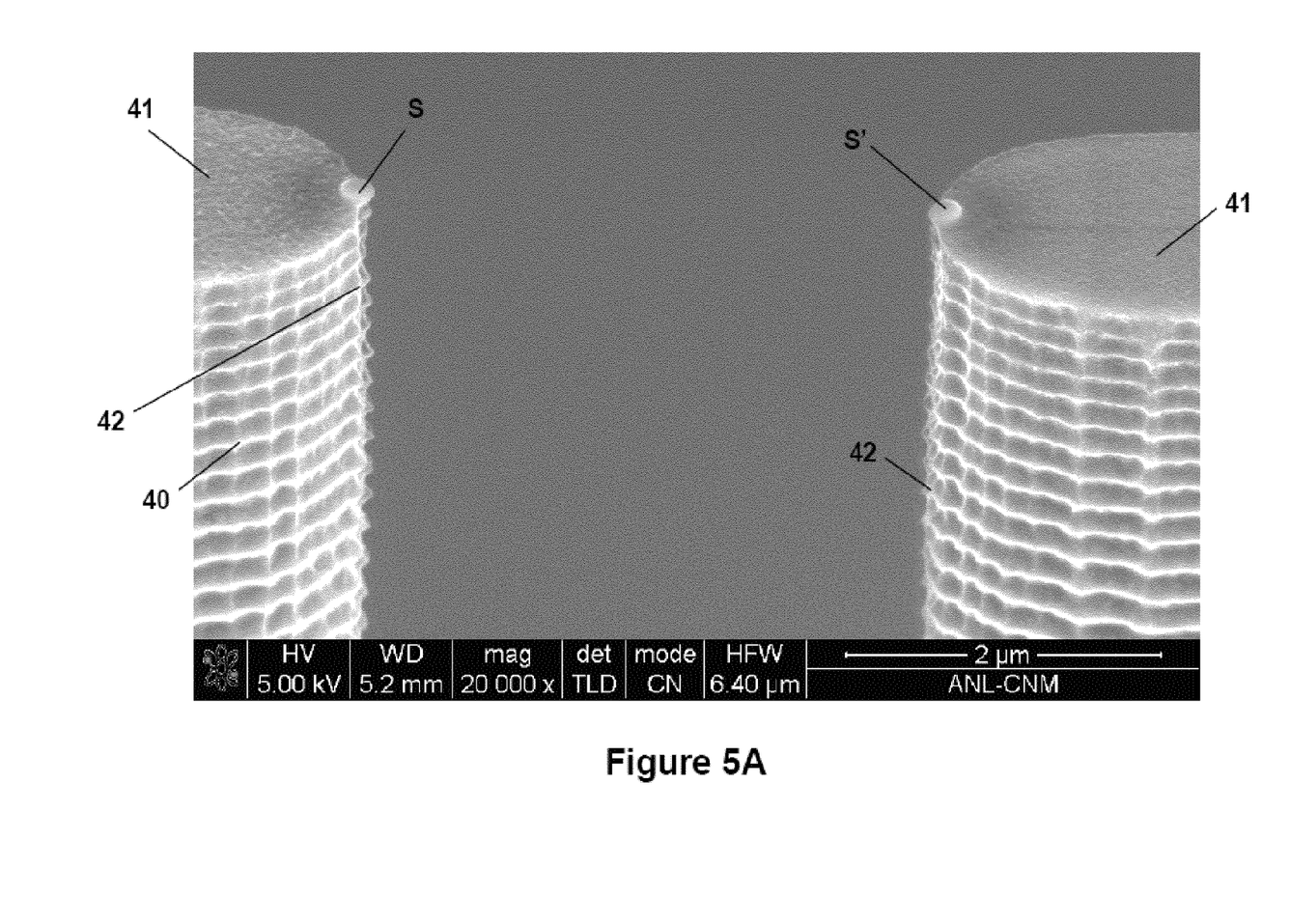
FIG. 5A is a detailed SEM image of a pair of MEMS nanoparticle positioning systems of FIG. 1 with a pair of attached nanospheres and FIG. 5B is a detailed and magnified SEM image showing a portion of the MEMS nanoparticle positioning systems of FIG. 5A.
Figure 5B:
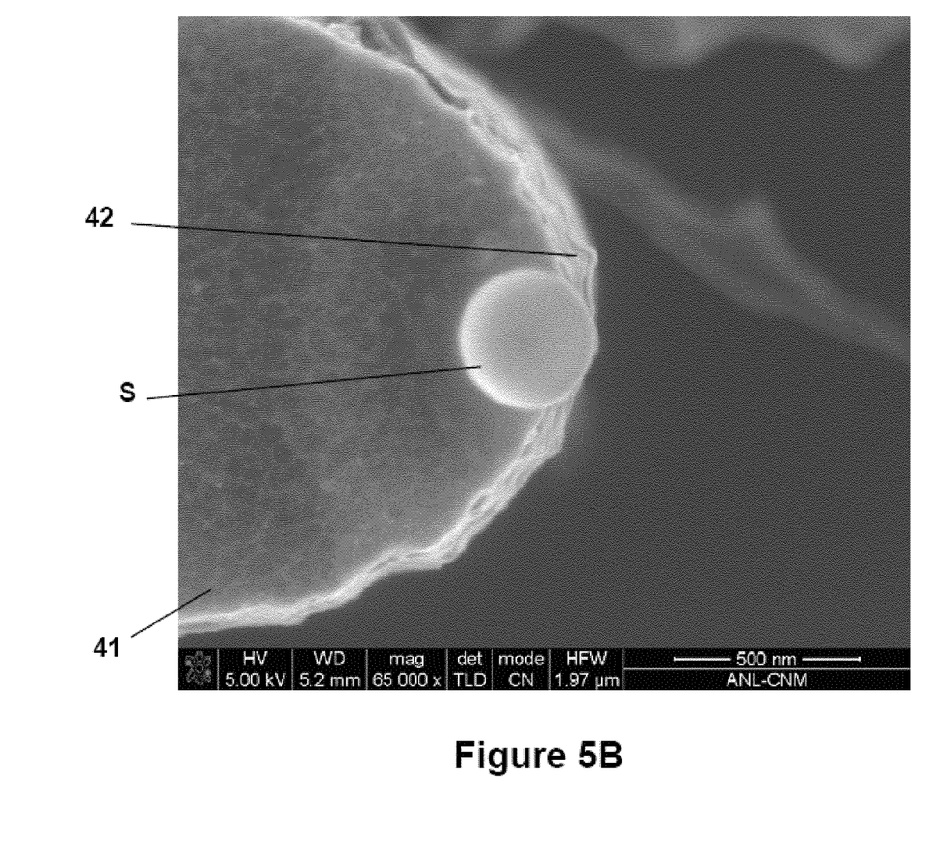

FIGS. 4A and 4B show a nanopyramid P located on an upper surface 41 of the micro-needle 40. FIGS. 5A and 5B depict a nanosphere S (or S') located on an upper surface 41 of the micro-needle 40.

Various nanostructures may be associated with the MEMS positioning system 10 using standard deposition tools. For example, electron beam lithography is one technique that may be used to form the desired nanostructure that may be associated with the MEMS positioning system 10. Alternatively, a focused ion beam technique may be used to directly deposit the nanostructure on the MEMS positioning system 10. As seen in FIGS. 3C, 4B and 5B, the various nanostructures 60 can be placed with a high degree of precision on the micro-needle 40, including proximate a distal edge 42. However, one or more nanostructures 60 may located anywhere on the micro-needle 40 or on another portion of the MEMS positioning system 10. The nanostructures can encompass a wide range of materials for various applications in sensing, nanooptics, and nanoelectronics. The various nanostructures that may be associated with the MEMS positioning system 10 may be constructed of any appropriate material or materials capable of forming a nanostructure. For example, nanostructures of various noble metals (e.g., Au, Ag, Pt, etc.), carbon and other materials may be constructed and associated with the MEMS positioning system 10. For instance, FIGS. 3A and 3B depict a pair of plasmonic Pt nanodots D/D'. FIGS. 4A and 4B show a pair Au nanopyramids P/P'. In various embodiments, nanostructures of different materials may be positioned relative to each other using one or more of the MEMS positioning systems 10.

A nanostructure MEMS positioning system may comprise two or more MEMS positioning systems 10 configured for interaction such that two or more nanostructures 60 may be selectively positioned with respect to each other. As depicted in FIGS. 3A-3C, a pair of MEMS positioning systems 10 are (see FIGS. 3A and 3B) opposingly arranged to locate a pair of nanodots D/D' (see FIG. 3C) in relation to each other. The boom 33 of the first MEMS positioning system 10 is substantially coaxial with the boom 33' of the second MEMS positioning system 10'. As such, axial displacement of the micro-needle 40 by the first MEMS positioning system 10 (substantially along the X axis) modulates the distance, i.e. increases or decreases the distance, between the nanodots D/D'. Alternatively, and/or in conjunction with the displacement of the first micro-needle 40 by the first MEMS positioning system 10, the second MEMS positioning system 10' may be actuated to cause an axial displacement of the respective micro-needle 40' substantially along the X axis. FIG. 3C shows the nanodots D/D' positioned to have a separation distance of about 2 μm. FIGS. 4A and 4B show the nanopyramids P/P' selectively positioned in proximity to each other such that the respective apexes of the nanopyramids P/P' are aligned. Accordingly, a tunable bow-tie nanoantenna is formed where operation of the nanoantenna may be selectively controlled by modulating the distance between the nanopyramids P/P'.

Additionally, the MEMS positioning systems 10 may be configured to modulate the position of the attached nanostructures in a second dimension, e.g. along the Y axis. For example, displacement in the second dimension, substantially normal to axial displacement along the X axis, is achieved via the lateral electrode 80 (see FIG. 1). As such, precise and reliable coupling of the nanoparticles may be achieved by approximating the MEMS positioning systems 10/10' relative to each other along the X and Y axes. Multi-axis positioning of the nanoparticles can produce a range of applications as described below, based on the control of the optical and electronic properties induced by closely spaced, interacting nanoparticles. Further, positioning control may be achieved by providing additional electrodes and or positioning elements as needed.

Figure 7:
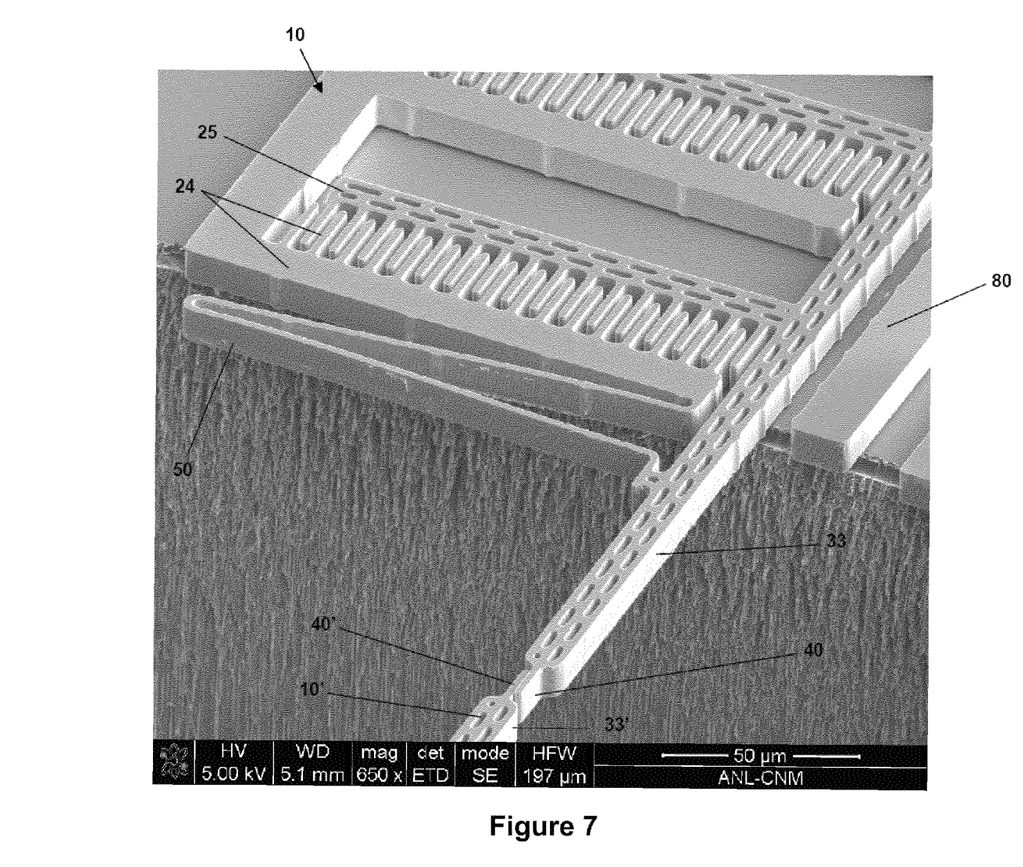
FIG. 7 is a SEM image of a portion of a pair of the MEMS nanoparticle positioning systems of FIG. 1.

In other embodiments, other nanostructure 60 placement configurations may be used, depending on, for example, the application and/or structure. For example, FIG. 7 shows an arrangement of a pair of MEMS positioning systems 10 and 10' (not fully shown) where the respective micro-needles 40/40' are configured to at least partially overlap. In the embodiment of FIG. 7, the booms 33/33' are substantially parallel and disposed in a plane but are laterally offset by a distance approximately equal to the width of one of the micro-needles 40/40'. In various embodiments the booms 33/33' may be coaxial and the lateral offset may be achieved by positioning one or more of the micro-needles 40/40' in the lateral (Y-axis) direction by imparting a displacement via the lateral electrode 80. In still other embodiments, two or more MEMS positioning systems 10 may be arranged in space as necessary to provide positioning control of a plurality of nanostructures.

The described embodiments may provide opportunities to develop new sensor technologies and switchable control of energy flow in various forms, e.g., optical, electronic, heat, etc. In particular, the present embodiments may be applied to create coupled plasmonic nanoparticles, a key element under development for opto-electronic applications, including sensors, communications, interconnects and wavefront control. The foregoing systems and methods have numerous applications, including, but not limited to:

An optical or plasmonic switch Plasmons are of significant interest for next generation sub-wavelength waveguides, but researchers currently do not have a reliable way to externally control the flow of plasmons between nanostructures. An optical or plasmonic switch may be constructed by, for example, bringing together a first plasmonic nanoparticle and a second plasmonic nanoparticle using the devices and methods already described. By modulating the distance between the first plasmonic nanoparticle and the second plasmonic nanoparticle, a shift in the resonance of the particles may be used as a nanoscale optical switch by varying the absorption at different wavelengths. According to the embodiments described herein, an electrically addressable plasmonic switch might be formed by modulating the distance between the nanostructures, i.e., decreasing the distance between the nanostructures to induce plasmon flow and then separating the nanostructures to turn off plasmon flow.

A spatial plasmon modulator A critical limitation in the area of optical interconnects is the absence of a technology to modulate optical signals that are smaller than the wavelength of the light used in the signal. Plasmons are electromagnetic waves localized in very small regions; but there is not a reliable method to manipulate plasmons in a controlled manner. Integration of metallic nanoparticles with MEMS or NEMS devices as in the described embodiments may allow for control of the relative amplitude or phase of various plasmons in arbitrary spatial locations. In doing so, an ideal device for applications like inter-chip optical interconnects may be constructed. Devices constructed according the various embodiments described herein may have the potential to reliably and controllably manipulate plasmons for such applications.

A sensor, and in a particular embodiment a surface enhanced Raman scattering (SERS) sensor Tuning the distance between nanoparticles according to embodiments described herein can optimize field confinement and enhancement effects that other SERS nanostructures cannot currently approach. By positioning molecules in this small region, molecular spectroscopy of a single molecule can be achievable through SERS techniques. The gains in field strength are not limited to SERS, as other material properties such as absorption and emission can be modified through controllable field enhancement by modulation of nanoparticle position.

Tunable nanoscale antennae Plasmonic antennae that can operate at the nanoscale are key to next generation nanophotonic structures. Antennae act to collect and confine electromagnetic waves for use in photonic devices. A "bow-tie" configuration, such as depicted in FIGS. 4A and 4B, is one such antenna structure and comprises two triangular structures with a gap between the apex of the two triangles. However, miniaturizing antennae structure for use in nanophotonics requires gaps to be formed that are generally too small to be constructed with current lithography technology. The embodiments described herein enable both a sufficiently small gap and selective tunability in the gap distance—for optimization of the antennae collection performance—to be achieved. It is expected that these structures may ultimately provide optical readout for on chip nanophotonic logic or routing light devices.

Nanoscale control of energy and charge transport In addition to plasmon coupling, new techniques to control energy and charge transport within nanostructures are needed. By placing energy or charge donors and acceptors on opposing nanopositioners, tunable control of energy and charge flow could be achieved. This applies to both organic and inorganic materials that are integrated with the nanopositioners.

Advanced heterodyne methods of detection Embodiments described herein could also enable the positioning of nanoparticles to be modulated through the use of an AC field and the ability to use lock-in detection of the modulated properties for extraordinarily enhanced signal to noise in sensing and spectroscopy applications.

Multiplexing Embodiments of the MEMS positioning devices described herein could permit multiplexing of a signal across multiple nanopositioners for parallel signal processing and achieve corresponding gains in efficiency for sensing and spectroscopy.

The foregoing description of embodiments of the present invention has been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments, and with various modifications, as are suited to the particular use contemplated.

What is claimed is:

1. A nanopositioning system for producing a coupling interaction between a first nanostructure and a second nanostructure, comprising:

a first microelectromechanical system (MEMS) positioning assembly, the first MEMS positioning assembly including a first static comb drive actuator and a first dynamic comb drive actuator, the first static comb drive actuator configured to selectively displace the first dynamic comb drive actuator along a first axis in relation to the first static comb drive actuator upon application of a first voltage to the first static comb-drive actuator;

a first restoring force element having a first end and a second end, the first end operatively connected to the first the dynamic comb drive actuator and the second end operatively connected to the first static comb drive actuator;

a first positioning electrode configured to selectively displace the first dynamic comb drive actuator along a second axis, perpendicular to the first axis, in relation to the first static comb drive actuator; and the first nanostructure operatively connected to the first dynamic comb drive actuator, a second MEMS positioning assembly, the second MEMS positioning assembly including a second static comb drive actuator and a second dynamic comb drive actuator, the second static comb drive actuator configured to selectively displace the second dynamic comb drive actuator along a third axis in relation to the second static comb drive actuator upon application of a second voltage to the second static comb-drive actuator;

a second restoring force element having a first end and a second end, the first end operatively attached to the second dynamic comb drive actuator and the second end attached to the second static comb drive actuator;

a second positioning electrode configured to selectively displace the second dynamic comb drive actuator along a fourth axis in relation to the second static comb drive actuator; and the second nanostructure operatively connected to the second dynamic comb drive actuator, the second nanostructure is selectively positionable along the third axis and along the fourth axis by operation of the second MEMS positioning assembly and the second positioning electrode to modulate the distance between the first nanostructure and the second nanostructure;

wherein the first nanostructure is selectively positionable along the first axis and along the second axis by operation of the first MEMS positioning assembly and the first positioning electrode to modulate a distance between the first nanostructure and the second nanostructure to obtain a plasmon coupling interaction that alters at least one property of the first nanostructure and the second nanostructure.

2. The nanopositioning system of claim 1, wherein the first axis and the third axis are substantially parallel.

3. The nanopositioning system of claim 2, wherein the second axis and the fourth axis are substantially parallel.

4. The nanopositioning system of claim 1, wherein the distance is selectively controllable to within about 1 nanometer.

5. The nanopositioning system of claim 1, wherein the at least one property is selected from the group consisting of optical properties and electrical properties.

6. The nanopositioning system of claim 5, wherein the at least one of an electrical property and an optical property comprises resonance shifting.

7. The nanopositioning system of claim 1, wherein the first MEMS positioning assembly includes a plurality of first static comb drive actuators forming a first static comb drive actuator assembly, and wherein the first dynamic comb drive actuator includes a plurality of first dynamic comb drive actuators forming a first dynamic comb drive actuator assembly.

8. The nanopositioning system of claim 7, further comprising a boom operatively connected to the first dynamic comb drive actuator assembly, wherein the first nanostructure is disposed on a surface of the boom.

9. A device comprising the nanopositioning system of claim 1, wherein the device is selected from the group consisting of: a plasmonic switch, an optical switch, a plasmon modulator, a surface enhanced Raman scattering sensor, a nanoscale antennae, a charge transport, a heterodyne sensor, and a multiplexer.

10. A nanopositioning system for modulating a distance between a first nanostructure and a second nanostructure to control an interaction between the first nanostructure and the second nanostructure, comprising:

a first nanopositioner configured to receive a first nanostructure, a second nanopositioner configured to receive a second nanostructure spaced a distance from the first nanostructure, each of the first nanopositioner and the second nanopositioner including a positioning portion selectively moveable along a respective first path by a first actuator and selectively moveable along a respective second path, which is orthogonal to the first path, by a second actuator to cause a plasmon coupling interaction between the first nanostructure and the second nanostructure, each of the first nanopositioner and the second nanopositioner further including a restoring force element coupled to the positioning portion, the restoring force element deformable in response to movement of the positioning portion along the respective first path, wherein a degree of the plasmon coupling interaction between the first nanostructure and the second nanostructure is selectively controllable and reversible by modulating the distance between the first nanostructure and the second nanostructure by movement of at least one of the first nanostructure and the second nanostructure along at least one of the respective first paths and the respective second paths.

11. The nanopositioning system of claim 10, wherein the distance between the first nanostructure and the second nanostructure is controllable to within about 1 nanometer of an intended distance.

12. The nanopositioning system of claim 10, wherein the coupling interaction between the first nanostructure and the second nanostructure causes at least one of an electrical property and an optical property of the first nanostructure and the second nanostructure to be altered.

13. The nanopositioning system of claim 10, wherein the coupling interaction between the first nanostructure and the second nanostructure is controllable in real time.

* * * * *